United States Patent [19]

Kurkov

[11] Patent Number: 4,504,486

[45] Date of Patent: Mar. 12, 1985

[54] 3-ISOXAZOLIN-5-ONE FUNGICIDES

[75] Inventor: Victor P. Kurkov, San Rafael, Calif.

[73] Assignee: Chevron Research Company, San Francisco, Calif.

[21] Appl. No.: 379,388

[22] Filed: May 17, 1982

[51] Int. Cl.³ .......................................... C07D 261/12
[52] U.S. Cl. .................................... 514/380; 548/243
[58] Field of Search ......................... 424/272; 548/243

[56] References Cited

U.S. PATENT DOCUMENTS 3,166,565  1/1965  Rigterink ............................ 548/243
3,629,430 12/1971  Takahi et al. ....................... 548/243

FOREIGN PATENT DOCUMENTS 2940189  4/1981  Fed. Rep. of Germany ...... 424/272
7116268  5/1972  Netherlands ....................... 424/272

OTHER PUBLICATIONS

Eckhard et al., ". . . Acyl Derivatives of Fungicide . . . ", *Chem. Abst.* 80: 141720y, (1974).

Noller, Carl, *Textbook of Organic Chemistry*, Saunders Co., Philadelphia, (1966), p. 431.
Ber. DT. Chem. Res., vol. 27: 1172, (1894).
Ber. DT. Chem. Res., vol. 44: 467–469, (1911).

*Primary Examiner*—Donald G. Daus
*Assistant Examiner*—G. Hendricks
*Attorney, Agent, or Firm*—S. R. LaPaglia; T. G. DeJonghe; L. S. Squires

[57] ABSTRACT

Compounds of the formula

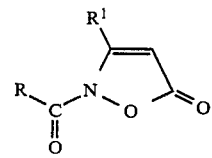

wherein R is phenyl or phenyl substituted with 1 to 3 of the same or different substituents selected from fluoro, chloro, bromo, iodo, nitro, lower alkyl, lower alkoxy or lower alkyl substituted with 1 to 3 of the same or different halogens; and $R^1$ is lower alkyl are good fungicides.

9 Claims, No Drawings

3-ISOXAZOLIN-5-ONE FUNGICIDES

BACKGROUND OF THE INVENTION

This invention pertains to novel fungicidal compounds. As the world becomes more dependent for food on an ever-decreasing acreage of farmland, effective fungicides which protect crops from fungicidal destruction are becoming increasingly important.

SUMMARY OF THE INVENTION

The compounds of the present invention are represented by the formula:

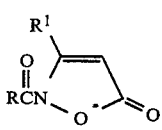

wherein R is phenyl or phenyl substituted with 1 to 3 of the same or different substituents selected from fluoro, chloro, bromo, iodo, nitro, lower alkyl, lower alkoxy or lower alkyl substituted with 1 to 3 of the same or different halogens; $R^1$ is lower alkyl or lower alkyl substituted with 1 to 3 of the same or different halogens.

Among other factors, the present invention is based on my finding that the compounds of this invention are effective fungicides.

In part, due to their superior fungicidal properties, preferred R groups include, for instance, mono and dihalosubstituted phenyls.

Particularly preferred R groups include 2,4-dihalophenyls.

Other preferred R groups include, for instance, the p-nitrophenyl and p-halophenyl groups.

Preferred halogens include bromo and chloro.

Preferred $R^1$ alkyl groups include, for instance, methyl, ethyl, n-propyl and the like.

DEFINITIONS

As used herein the following terms have the following meanings unless expressly stated to the contrary. The term "alkyl" refers to both straight- and branched-chain alkyl groups. The term "lower alkyl" refers to both straight- and branched-chain alkyl groups having a total of 1 through 6 carbon atoms and includes primary, secondary and tertiary alkyl groups. Typical lower alkyls include, for example, methyl, ethyl, n-propyl, isopropyl, n-butyl, t-butyl and the like.

The term "alkoxy" refers to the group $R^3O$— wherein $R^3$ is alkyl.

The term "lower alkoxy" refers to alkoxy groups having from 1 to 6 carbon atoms; examples include methoxy, ethoxy, hexoxy and the like.

The term "halo" or "halogen" refers to the groups fluoro, chloro, bromo and iodo.

The term "3-isoxazolin-5-one" refers to the group:

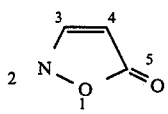

with the conventional numbering system employed. Thus, the term "2-(2',4'-dichlorobenzoyl)-3-isoxazolin-5-one" refers to the group:

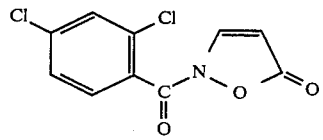

DETAILED DESCRIPTION OF THE INVENTION

The compounds of the present invention are prepared according to the following reaction scheme:

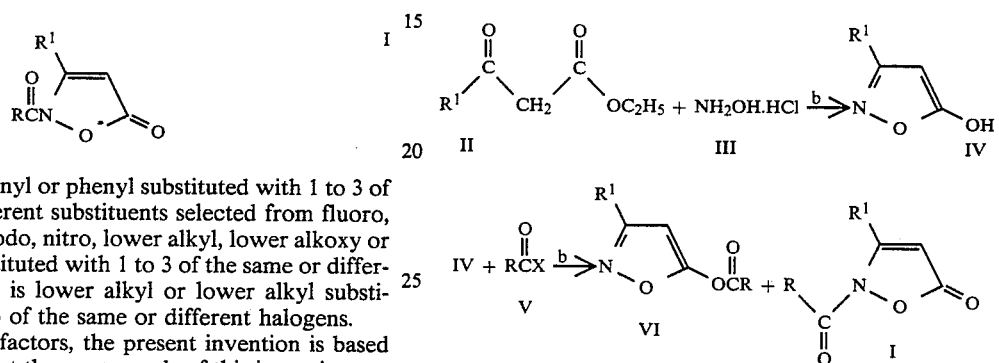

where R and $R^1$ are as defined above, b represents a base and X is a halogen.

Reaction (1) is a known condensation reaction and is described in J. Gen. Chem., (USSR) 10, 557–68 (1940), CA 34:7903 (1940) which is incorporated herein by reference. The reaction is preferably accomplished by adding an essentially equimolar amount of hydroxylamine hydrochloride to II. An essentially equimolar amount of a base, b, is then added to the system to scavenge the acid present. The base employed may be either an organic or inorganic base. Suitable organic bases include, for instance, trialkylamines (e.g. triethylamine), pyridine and the like. Suitable inorganic bases include, for instance, sodium methoxide, sodium carbonate and the like. The reaction is generally conducted in the liquid phase employing an organic solvent such as methanol, ethanol, and the like. Preferably, the reaction is conducted in ethanol using sodium methoxide as the base. Alternatively, in lieu of a solvent, an excess of an organic base such as pyridine is employed. Reaction pressure is not critical and for convenience the reaction is generally conducted at atmospheric pressure. The reaction is generally conducted at from 0° C. to 80° C. and is generally complete from within 1 to 24 hours. The 5-hydroxy-3-substituted isoxazole, IV, is then isolated by conventional procedures such as extraction, filtration, chromatography, distillation or alternatively is used directly in reaction (2) without purification and/or isolation. Caution should be exercised in distilling the isoxazoles, IV, as violent explosions are possible.

Reaction (2) is conducted by adding an essentially equimolar amount of the appropriate acid halide, V, to IV. Optionally, an essentially equimolar amount of a base, b, is added to the system to scavenge the acid generated by the reaction. The base employed may be either an organic base or an inorganic base. Suitable organic bases include, for instance, trialkylamines (e.g. triethylamine), pyridine and the like. Suitable inorganic bases include, for instance, sodium methoxide, sodium carbonate and the like. The reaction is generally conducted in the liquid phase employing an anhydrous organic solvent such as chloroform, toluene and the like. Alternatively, in lieu of a solvent, an excess of the acid halide, V, is employed. When conducting the reaction under such conditions, a base is not employed. Reaction pressure is not critical and for convenience the reaction is generally conducted at atmospheric pressure. The reaction is generally conducted at from 0° C. to 150° C. and is generally complete from within 1 to 24 hours. The reaction produces 2 products: the desired 3-isoxazolin-5-one products and the 5-hydroxyisoxazole esters, VI. The desired product, I, is then isolated by conventional procedures such as extraction, filtration chromatography, distillation and the like.

UTILITY

The compounds of the present invention are useful for controlling fungi. Additionally, some of the compounds are useful in controlling leaf blights caused by organisms such as *Phytophthora infestans conidia, Alternaria solani conidia, Septoria apii,* downy mildew caused by organisms such as *Plasmopara viticola,* powdery mildew caused by organisms such as *Erisiphe polygoni* and other fungal infections caused by organisms such as *Botrytis cinerea, Rhizoctania solani* and *Pythium ultimum.*

However, some fungicidal compounds of the invention may be more fungicidally active than others against particular fungi. Table II and II (a) lists a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any several other known types of formulations, depending on the desired mode of application.

Wettable powders are in the form of finely divided particles which disperse readily in water or other dispersant. These compositions normally contain from about 5% to 80% fungicide, and the rest inert material, which includes dispersion agents, emulsifying agents and wetting agents. The powder may be applied to the soil as a dry dust, or preferably as a suspension in water. Typical carriers include fuller's earth, kaolin clays, silicas, and other highly absorbent, readily wettable, organic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bacteriocides, plant growth regulator, fertilizers, etc.

A further understanding of the invention can be had in the following non-limiting Examples. Wherein, unless expressly stated to the contrary, all temperatures and temperature ranges refer to the centigrade system and the term "ambient" or "room temperature" refers to about 20° C. to 25° C. The term "percent" refers to weight percent and the term "mol" or "mols" refers to gram mols. The term "equivalent" refers to a reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products.

EXAMPLE 1

Preparation of 3-methyl-3-isoxazolin-5-one

To 30 gm of ethyl acetoacetate in 80 ml of absolute ethanol was added 16 gm of hydroxylamine hydrochloride. 12.4 gm of sodium methoxide was then added and the system stirred at room temperature for five hours. The ethanol was removed by stripping and the residue dissolved in methylene chloride. The methylene chloride solution was washed with water and dried over magnesium sulfate. The methylene chloride was removed by stripping to give 20 gm of an orange oil. The 3-methyl-3-isoxazolin-5-one was purified by distillation. 9 gm of the 3-methyl-3-isoxazolin-5-one was obtained at 82° C. and approximately ~0.1 mm Hg. Caution: During one distillation a violent exothermic reaction occurred.

EXAMPLE 2

Preparation of 3-n-propyl-3-isoxazolin-5-one

To 63.3 gm of 3-ketohexanoic acid ethyl ester was added 30.6 gm of hydroxylamine hydrochloride. 23.7 gm of sodium methoxide was then added and the system stirred at room temperature for 20 hours. The ethanol was removed by stripping and the residue then dissolved in methylene chloride. The methylene chloride was washed with water and dried over magnesium sulfate. The methylene chloride was removed by stripping to give 54.8 gm of the 3-n-propyl-b 3-isoxazolin-5-one.

EXAMPLE 3

Preparation of 3-methyl-2-(4'-nitrobenzoyl)-3-isoxazolin-5-one 4 gm of 3-methyl-3-isoxazolin-5-one was added to 20 ml of toluene along with 3.5 gm of pyridine. 8.2 gm of 4-nitrobenzoyl chloride in 80 ml of toluene was added dropwise. The solution was stirred at room temperature for 4 hours. Afterwards, the system was poured into 200 ml water. The resulting solution was filtered and the organic phase then separated and dried over sodium sulfate. The toluene was removed by stripping to give 6.9 gm of a mixture of 3-methyl-2-(4'-nitrobenzoyl)-3-isoxazolin-5-one and 3-methyl-5-hydroxyisoxazolyl4'-nitrobenzoate. The crude product was recrystallized in ethanol to give 4.6 gm of the mixture. The product 3-methyl-2-(4-nitrobenzoyl)-3-isoxazolin-5-one was separated by column chromatography using 200 gm of E.M. silica gel 60 in an 80×90 mm column and a 2% solution of acetone in methylene chloride as the elutant. Listed as compound number 1, Table I.

EXAMPLE 4

Preparation of 3-methyl-2-(2',4'-dichlorobenzoyl)-3-isoxazolin-5-one 20.9 gm of 2,4-dichlorobenzoyl chloride was added to 5 gm of 3-methyl-3-isoxazolin-5-one. The reaction mixture was heated at 150° C. for 3 hours. The reaction was neutralized with 100 ml of saturated sodium bicarbonate solution and extracted with methylene chloride. The organic layer was separated, washed with water, dried over anhydrous sodium sulfate and filtered. The solvent was stripped to yield 32.6 gm of the crude product. The product was recrystallized from methylene chloride-hexane yielding 6.4 gm, m.p. 137°–139° C.

EXAMPLE 5

Preparation of 3-n-propyl-2-(2',4'-dichlorobenzoyl)-3-isoxazolin-5-one 20.9 gm of 2,4-dichlorobenzoyl chloride was added to 8 gm of 3-n-propyl-3-isoxazolin-5-one. The system was heated at 100° C. for 3 hours. Afterwards, the system was neutralized with 150 ml of saturated sodium bicarbonate solution. The product was extracted with methylene chloride. The organic solution was washed with saturated sodium bicarbonate solution, dried over magnesium sulfate and filtered. The organic solution was stripped to yield 28.8 gm of the crude product as a brown oil. The product was purified by HPLC using 1:3 tetrahydrofuran/hexane as the eluant to yield the title compound as a brown solid, m.p. 63°–65.5° C.

Other compounds which are prepared in accordance with Examples 1 to 5 above include for instance:
3-n-propyl-2-(2',4'-dibromobenzoyl)-3-isoxazolin-5-one;
3-ethyl-2-(3',5'-dibromobenzoyl)-3-isoxazolin-5-one;
3-methyl-2-(4'-fluorobenzoyl)-3-isoxazolin-5-one;
3-m-hexyl-2-(4'-iodobenzoyl)-3-isoxazolin-5-one;
3-methyl-2-(4'nitrobenzoyl)-3-isoxazolin-5-one;
3-ethyl-2-(2'-chloro-4'-nitrobenzoyl)-3-isoxazolin-5-one;
3-ethyl-2-(4'-trifluoromethylbenzoyl)-3-isoxazolin-5-one;
3-ethyl-2-(4'-methylbenzoyl)-3-isoxazolin-5-one;
3-ethyl-2-(4'-methoxybenzoyl)-3-isoxazolin-5-one; and
3-isopropyl-2-(2',4',6'-trichlorobenzoyl)-3-isoxazolin-5-one.

EXAMPLE 6

Leaf Rust

The Leaf Rust test was made using pinto beans. The pathogen was *Uronyces phaseoli tipica*. The pinto bean plants were sprayed with a 250 ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

EXAMPLE 7

Tomato Late Blight

Compounds of the invention were tested for the preventative control of the Tomato Late Blight organism *Phytophthora infestans*. Five- to six-week old tomato (cultivar Bonny Best) seedlings were used. The tomato plants were sprayed with a 250 ppm suspension of the test compound in acetone, water and a small amount of a nonionic emulsifier. The sprayed plants were then inoculated one day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II. In Table II, the test concentration is 250 ppm unless otherwise indicated by the figures in parentheses.

EXAMPLE 8

Celery Late Blight

The Celery Late Blight tests were conducted using celery (Utah) plants 11 weeks old. The Celery Late Blight organism was *Septoria apii*. The celery plants were sprayed with 250 ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table II.

EXAMPLE 9

Grape Downy Mildew Control

The compounds of the invention were tested for the control of the Grape Downy Mildew Control organism *Plasmopara viticola*. Detached leaves, between 70 and 85 mm in diameter, of 7-week old *Vitis vinifera* cultivar Emperor grape seedlings were used as hosts. The leaves were sprayed with a 250 ppm solution of the test compound in acetone. The sprayed leaves were dried, inoculated with a spore suspension of the organism, placed in a humid environmental chamber and incubated at 66° to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE 10

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated 1 day later with the organism, placed in the environmental chamber and incubated at 66° to 68° F. and 100% relative humidity for 24 hours. Following the incubation, the plants were maintained in a greenhouse for about 12 days. Percent diseases control was based on the percent disease development on untreated check plants. The compounds tested and the results are tabulated in Table II.

EXAMPLE 11

Bean Powdery Mildew

The compounds of the invention were tested for the control of the Bean Powdery Mildew organism *Erisiphe polygoni*. Seedling bean plants were sprayed with a 250 ppm solution of the test compound in acetone, water and a nonionic emulsifier. The sprayed plants were then inoculated 1 day later with organism. The plants were maintained for 10 days at temperatures of 68° F. at night with daytime temperatures of 72° to 80° F.; relative humidity was maintained at 40% to 60%. The percent disease control provided by a given test compound was based on the percent disease reduction relative to the untreated check plants. The results are tabulated in Table II.

EXAMPLE 12

Mycelial Inhibition

The compounds of the present invention were evaluated for in-vitro fungicidal effectiveness by means of a Mycelial Inhibition test. This test is designed to measure the fungitoxic activity of fungicidal chemicals in terms of their degree of inhibition of mycelium growth. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip. The effectiveness of the compounds tested for fungicidal activity is reported in Table II (a) for those compounds which were effective in inhibiting mycelial growth.

The activity is reported in terms of $$\frac{\text{micrograms/cm}^2 \text{ for 99\% control of the fungus for the standard}}{\text{micrograms/cm}^2 \text{ for 99\% control of the fungus for the test compound}} \times 100$$

When more than 1.6 micrograms/cm$^2$ for 99% control of the fungus for the test compound is required, the activity is reported as 0.

EXAMPLE 13

Rice Blast

Compounds of this invention were tested for control of the Rice Blast organism, *Piricularia oryzae*, using 10- to 14-day old rice plant seedlings (Calrose M-9 variety). Seedling plants were sprayed with a 625 ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on untreated check plants:

$$\% \text{ Control} = 100 \times \left( \frac{\% \text{ disease in treated plants}}{\% \text{ disease in check}} \right)$$

The results are tabulated in Table II.

TABLE I

Compounds of the Formula

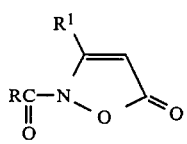

| Compound No. | R | R¹ | Carbon Calc. | Carbon Found | Hydrogen Calc. | Hydrogen Found | Nitrogen Calc. | Nitrogen Found | Form | m.p. |
|---|---|---|---|---|---|---|---|---|---|---|
| 1 | $O_2N$—C₆H₄— | $CH_3$ | 53.23 | 52.94 | 3.25 | 3.36 | 11.29 | 10.99 | yellow solid | 179–180° C. |
| 2 | 2,4-Cl₂-C₆H₃— | $CH_3$ | 48.6 | 48.7 | 2.6 | 2.9 | 5.2 | 5.2 | cream solid | 137–139° C. |
| 3 | 2,4-Cl₂-C₆H₃— | $CH_3CH_2CH_2$— | 52.02 | 51.84 | 3.69 | 3.79 | 4.67 | 4.78 | brown solid | 63–65.5° C. |
| 4 | C₆H₅— | $CH_3$ | 65.02 | 64.02 | 6.89 | 6.59 | 4.46 | 4.71 | orange solid | 59–66° C. |
| 5 | 2,4-Cl₂-C₆H₃— | $(CH_3)_2CH$— | 52.02 | 52.09 | 3.69 | 3.75 | 4.67 | 4.89 | yellow crystals | 108–109° C. |
| 6 | Cl—C₆H₄— | —$CH_3$ | 55.60 | 55.08 | 3.93 | 3.32 | 5.90 | 5.15 | tan solid | 128°–129° C. |
| 7 | 2-Cl-4-$O_2N$-C₆H₃— | —$CH_3$ | 46.74 | 46.76 | 2.50 | 3.04 | 9.91 | 9.63 | tan solid | 89.5°–92° C. |
| 8 | 4-Cl-2-$NO_2$-C₆H₃— | —$CH_3$ | 46.74 | 47.20 | 2.50 | 2.54 | 9.91 | 9.80 | tan solid | 178°–179° C. |

TABLE II

FUNGICIDAL ACTIVITY
% Control

| Compound Number | GDM | TLB | CLB | TEB | BPM | Rice Blast | BR |
|---|---|---|---|---|---|---|---|
| 1 | 21 | 0 | — | 0 | 0 | — | 0 |
| 2 | 14 | 97 | 99 | 92 | 21 | — | 0 |
| 3 | 0 | 35 | 0 | — | 0 | 44 | 0 |
| 4 | 6 | 50 | 0 | — | 0 | 0 | 0 |
| 5 | 3 | 69 | 0 | — | 0 | 83 | 0 |
| 6 | 16 | 50 | 0 | 0 | 0 | 0 | 0 |
| 7 | 19 | 31 | 44 | 0 | 0 | 50 | 0 |
| 8 | 6 | 56 | 11 | 56 | 0 | 0 | 0 |

GDM = Grape Downy Mildew (*Plasmopara viticola*)
TLB = Tomato Late Blight (*Phytophthora infestans*)
CLB = Celery Late Blight (*Septorii apii*)
TEB = Tomato Early Blight (*Alternia solani conida*)
BPM = Bean Powdery Mildew (*Erisiphe polygoni*)
Rice Blast = (*Piricularia oryzae*)
BR = Bean Rust (*Uronyces phaseoli tipica*)

TABLE II (a)

FUNGICIDAL ACTIVITY
IN TERMS OF MYCELIAL INHIBITION
% Standard

| Compound Number | Botrytis | Pythium | Rhizoc. |
|---|---|---|---|
| 1 | 0 | 0 | 0 |
| 2 | 34 | 0 | 0 |
| 3 | 0 | — | 0 |
| 4 | 0 | — | 0 |
| 5 | 0 | — | 23 |
| 6 | 6 | 12 | 33 |
| 7 | 0 | 0 | 0 |
| 8 | 15 | 0 | 0 |

Botrytis - *Botrytis cinerea*
Pythium - *Pythium ultimum*
Rhizoc. - *Rhizoctania solani*
Standard - DIFOLATAN ®

What is claimed is:
1. A compound of the formula

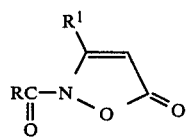

wherein R is phenyl or phenyl substituted with 1 to 3 of the same or different substituents selected from fluoro, chloro, bromo, iodo, nitro, lower alkyl having 1 through 6 carbon atoms, lower alkoxy having 1 through 6 carbon atoms or lower alkyl, having 1 through 6 carbon atoms, substituted with 1 to 3 of the same or different halogens; $R^1$ is lower alkyl having 1 through 6 carbon atoms.

2. A compound of the formula defined in claim 1 wherein R is phenyl substituted with 1 to 3 substituents selected from fluoro, chloro, bromo, iodo and nitro.

3. A compound of the formula defined in claim 2 wherein R is 2,4-dichlorophenyl.

4. A compound of the formula defined in claim 2 wherein R is 4-nitrophenyl.

5. A compound of the formula defined in claim 3 wherein $R^1$ is methyl.

6. A compound of the formula defined in claim 4 wherein $R^1$ is methyl.

7. A method for the control of fungi which comprises applying thereto a fungicidally effective amount of the compound defined in claim 1.

8. A fungicidal composition comprising a biologically inert carrier and a fungicidally effective amount of the compound defined in claim 1.

9. The compound of claim 1 wherein R is monohalophenyl or dihalophenyl.